United States Patent [19]

Siegrist et al.

[11] Patent Number: 4,727,187

[45] Date of Patent: Feb. 23, 1988

[54] PROCESS FOR THE PREPARATION OF α,α-DIFLUOROALKYL PHENYL ETHER DERIVATIVES

[75] Inventors: Urs Siegrist, Möhlin; Jean Indermühle, Basel; Peter Baumeister, Flüh, all of Switzerland

[73] Assignee: Ciba-Geigy Corporation, Ardsley, N.Y.

[21] Appl. No.: 741,387

[22] Filed: Jun. 5, 1985

[30] Foreign Application Priority Data

Jun. 15, 1984 [CH] Switzerland ............. 2918/84
Jun. 15, 1984 [CH] Switzerland ............. 2917/84
Feb. 20, 1985 [CH] Switzerland .............. 790/85

[51] Int. Cl.[4] .............. C07C 43/225; C07C 149/34; C07C 149/425; C07C 143/80
[52] U.S. Cl. ........................... 564/89; 564/85; 564/86; 564/87; 564/90; 568/655; 568/656; 570/127
[58] Field of Search ............ 564/89, 85, 86, 87, 564/90; 568/655, 656; 570/127

[56] References Cited

U.S. PATENT DOCUMENTS

| | | | |
|---|---|---|---|
| 2,471,830 | 5/1949 | McBee et al. ............ | 568/655 |
| 2,803,665 | 7/1957 | Miller et al. | |
| 4,155,940 | 5/1979 | Marhold et al. ........... | 570/127 |
| 4,207,266 | 6/1980 | Opie ............... | 568/655 |
| 4,367,348 | 1/1983 | Simon-Birrenbaum et al. ... | 570/127 |
| 4,562,286 | 12/1985 | Foster ................. | 570/127 |
| 4,575,571 | 3/1986 | Desbois et al. ........... | 568/656 X |

FOREIGN PATENT DOCUMENTS

| | | | |
|---|---|---|---|
| 23422 | 7/1980 | European Pat. Off. . | |
| 44808 | 7/1981 | European Pat. Off. . | |
| 84743 | 6/1982 | European Pat. Off. . | |
| 1000393 | 1/1957 | Fed. Rep. of Germany ...... | 568/655 |

OTHER PUBLICATIONS

Houben-Weyl, *Methoden der Organischen Chemie*, Band v/3, pp. 132-133.
Chem. Abstract, vol. 71, (1969), 60927H.
Chem. Abstract, vol. 70, (1969), 3436C.
Organic Reaction, vol. 21, (1974), pp. 3, 111 and 112.
J. Fluorine Chemistry, vol. 24, (1984), pp. 191 to 192 and 202 to 203.

*Primary Examiner*—Anton H. Sutto
*Assistant Examiner*—Carolyn S. Greason
*Attorney, Agent, or Firm*—Michael W. Glynn; Irving M. Fishman

[57] ABSTRACT

The present invention relates to a novel process for the preparation of an α,α-difluoroalkyl phenyl ether of formula I

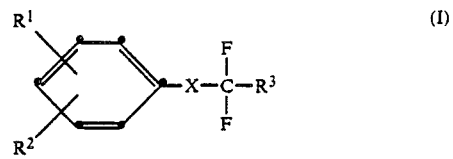

wherein
$R^1$ is hydrogen, halogen, amino, nitro, $-SO_2-R^4$, $-S-R^5$, $-SO-R^6$ or $-S-S-R^7$,
$R^2$ is hydrogen, halogen, nitro, hydroxy or $-SO_2-R^8$,
$R^3$ is $C_1-C_5$haloalkyl,
X is oxygen, sulfur, $-SO-$ or $-SO_2-$,
$R^4$ is hydroxy, halogen, amino, $-N=C=O$, $-NH-CO-Cl$, $-NH-CO-Br$, $-NR^9R^{10}$, benzyl, phenyl, $C_1-C_4$alkyl or $-NH'CO-NR^{11}R^{12}$,
$R^5$ and $R^6$ are $C_1-C_4$alkyl, phenyl or benzyl,
$R^7$ is $C_1-C_4$alkyl, phenyl or benzyl,
$R^8$ is hydroxy or halogen,
$R^9$ and $R^{10}$ are each independently of the other $C_1-C_4$alkyl or benzyl and
$R^{11}$ and $R^{12}$ are each independently of the other hydrogen, $C_1-C_4$alkyl, phenyl or an aromatic heterocycle, which process comprises fluorinating a compound of formula II

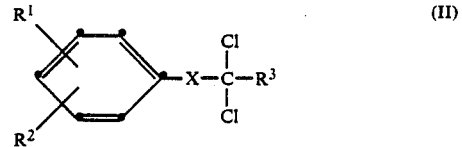

wherein $R^1$, $R^2$, $R^3$ and X are as defined for formula I, with hydrogen fluoride, in the presence of a catalytic amount of an antimony(V) compound. The intermediate of formula III

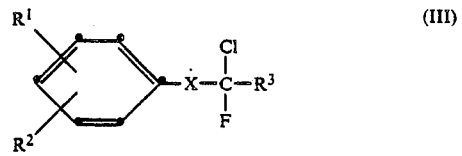

obtained when carrying out said process may, if desired, be isolated by selecting suitable reaction conditions.

23 Claims, No Drawings

PROCESS FOR THE PREPARATION OF α,α-DIFLUOROALKYL PHENYL ETHER DERIVATIVES

The present invention relates to a novel process for the preparation of α,α-difluoroalkyl phenyl ether derivatives and α-chloro-α-fluoroalkyl phenyl ether derivatives, and to novel α-chloro-α-fluoroalkyl phenyl ether derivatives.

The α,α-difluoroalkyl phenyl ether derivatives and α-chloro-α-fluoroalkyl phenyl ether derivatives which can be obtained by the novel process of the present invention are valuable intermediates for herbicidal and plant growth regulating compounds. Such compounds and their biological properties are described for example in European published applications 23 422 and 44 808. Furthermore, the α-chloro-α-fluoroalkyl phenyl ethers are intermediates for α,α-difluoroalkyl phenyl ether derivatives, which in turn are likewise starting materials for herbicidal sulfonyl ureas.

The production of compounds having α,α-difluoroalkyl phenyl ether structure has already been described in various publications: Organic Reactions, Vol. 21 (1974), Wiley, 1–124; J. Fluorine Chem. 24 (1984), 191–203; U.S. Pat. No. 2 803 665; or European published application No. 84 743. The processes employed do not prove very suitable for large-scale industrial application since, on the one hand, expensive starting materials are used and, on the other hand, only thioethers can be produced; or, on the one hand, substances are used which are problematical to handle and necessitates the use of complicated apparatus and, on the other hand, some of the reaction products are obtained in unsatisfactory purity.

There is therefore a need for a broadly applicable synthesis for the preparation of α,α-difluoroalkyl phenyl ether derivatives, which synthesis affords homogeneous products in high yield using inexpensive starting materials and avoiding complicated apparatus.

The preparation of compounds having α-chloro-α-fluoroalkyl ether structure has also already been described: Zh. Obshch. Khim. 1969, 39(4), 765–762 [C.A. 71 (1969) 60927h] or Zh. Obshch. Khim. 1969, 38(7), 1503–1509 [C.A. 70 (1969) 3436c]. Likewise, the processes employed do not prove very suitable for large-scale industrial application since, on the one hand, only mixtures of products of differing isomeric structure can be prepared and, on the other hand, only thioethers can be produced.

Here, too, there is therefore a need for a broadly applicable synthesis for the preparation of α-chloro-α-fluoroalkyl phenyl ether derivatives, which synthesis affords homogeneous products in high yield using inexpensive starting materials and avoiding complicated apparatus.

Surprisingly, it has now been found that the novel process of the present invention for the preparation of α,α-difluoroalkyl phenyl ether derivatives substantially meets current requirements and, by slightly modifying the reaction conditions, is at the same time suitable for the preparation of α-chloro-α-fluoroalkyl phenyl ether derivatives and here, too, fulfills the current requirements of a process suitable for large-scale manufacture.

The present invention relates to a process for the preparation of an α,α-difluoroalkyl phenyl ether derivative of formula I

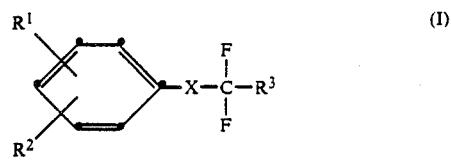

wherein
$R^1$ is hydrogen, halogen, amino, nitro, $-SO_2-R^4$, $-S-R^5$, $-SO-R^6$ or $-S-S-R^7$,
$R^2$ is hydrogen, halogen, nitro, hydroxy or $-SO_2-R^8$,
$R^3$ is $C_1-C_5$haloalkyl,
X is oxygen, sulfur, $-SO-$ or $-SO_2-$,
$R^4$ is hydroxy, halogen, amino, $-N=C=O$, $-NH-CO-Cl$, $-NH-CO-Br$, $-NR^9R^{10}$, benzyl, phenyl, $C_1-C_4$alkyl or $-NH-CO-NR^{11}R^{12}$,
$R^5$ and $R^6$ are $C_1-C_4$alkyl, phenyl or benzyl,
$R^7$ is $C_1-C_4$alkyl, phenyl or benzyl,
$R^8$ is hydroxy or halogen,
$R^9$ and $R^{10}$ are each independently of the other $C_1-C_4$alkyl or benzyl and
$R^{11}$ and $R^{12}$ are each independently of the other hydrogen, $C_1-C_4$alkyl, phenyl or an aromatic heterocycle,
which process comprises fluorinating a compound of formula II

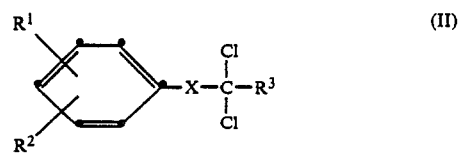

wherein $R^1$, $R^2$, $R^3$ and X are as defined for formula I, with hydrogen fluoride, in the presence of a catalytic amount of an antimony(V) compound.

In the definitions of formula I, halogen as substituent is fluorine, chlorine, bromine or iodine, preferably fluorine or chlorine. Halogen as moiety of haloalkyl has the same meaning and preferences.

Alkyl is e.g. methyl, ethyl, isopropyl, n-propyl, the four butyl isomers and the pentyl isomers.

By analogy, haloalkyl is in general preferably chloromethyl, fluoromethyl, chloroethyl, fluoroethyl, dichloromethyl, difluoromethyl, trichloromethyl, trifluoromethyl, trichloroethyl, trifluoroethyl, tetrachloroethyl, tetrafluoroethyl, perchloroethyl, perfluoroethyl, perfluoropropyl, perfluorobutyl or perfluoropentyl.

Within the scope of the present invention, aromatic heterocycles are unsubstituted or substituted triazole, triazine or pyrimidine rings, in particular 1,2,4-triazol-3-yl, 1,3,5-triazin-2-yl and 2-pyrimidinyl ring systems which are preferably substituted by two lower alkyl, lower alkoxy, halo-lower alkyl or halo-lower alkoxy groups.

The reaction products of formula I are either themselves herbicidal sulfonylureas or they can be converted into herbicidal sulfonylureas by one or more reaction steps which are known per se. Thus, compounds of formula I, wherein $R^1$ is the radical $-SO_2-NH-CO-NR^{11}R^{12}$, where $R^{11}$ or $R^{12}$ is a pyrimidine or triazine ring, are themselves herbicidal sulfonylureas. If $R^1$ is another sulfonic acid derivative, e.g. the free acid, an acid amide, an acid halide, an isocyanatosulfonyl radical or a carbamoylsulfonyl radical, then said derivatives can be converted into sulfonylurea derivatives by reaction methods which are known per se. Various methods are also known to the skilled person enabling him to convert compounds of formula I, wherein $R^1$ is hydrogen, halogen, amino, nitro, $—S—R^5$, $—SO—R^6$ or $—S—S—R^7$, into phenylsulfonic acid derivatives and subsequently into herbicidal sulfonylureas.

The fluorination catalyst used for carrying out the process (II→I) of the present invention is an antimony compound in which the antimony atom is present in oxidation state V. Compared with known processes, the use of this catalyst makes it possible at the same time to employ the relatively easily accessible hydrogen fluoride as fluorinating agent and to lower the reaction temperature. The lowering of the reaction temperature and the concomitant decrease in pressure result in a reduction of operating costs of the reactor. In favourable circumstances, the reaction may be carried out under normal pressure or under slight vacuum. In addition, the process of the present invention affords a higher yield of α,α-difluorinated product of formula I than obtained by the known processes.

It is preferred to use an antimony(V) halide as fluorination catalyst. Antimony pentachloride is particularly preferred on account of its ready accessibility. Catalyst systems which form antimony(V) compounds as intermediates are also suitable. Examples of such catalyst systems are mixtures of antimony trichloride and a halogen. To be specifically mentioned here is the mixture of antimony trichloride and bromine.

The proportion of catalyst in the reaction mixture can vary within wide limits. The reaction of the present invention can be carried out using 0.1 to 50 mol% of antimony(V) compound, based on the amount of starting material of formula II employed. Reaction rates suitable for industrial application in a large-scale reactor are attained by using as catalyst 1 to 20 mol%, preferably 5 to 20 mol%, of antimony(V) halide.

By using the novel fluorination catalyst, it is possible to carry out the reaction under mild reaction conditions, i.e., at relatively low reaction temperature. Accordingly, the reaction temperature is generally in the range from $-20°$ C. to $+100°$ C. It is preferred to keep the reaction temperature in the range from $-10°$ C. to $+20°$ C.

The hydrogen fluoride employed as fluorinating agent is used in at least equivalent amount. Generally, an excess of hydrogen fluoride of 0.5 to 2 mol is used. The reaction may be carried out without a solvent or in the presence of an inert solvlent. Suitable inert solvents are: amides such as dimethylformamide or N-methylpyrrolidone; aromatic hydrocarbons such as benzene, toluene or xylene; sulfoxides such as dimethylsulfoxide; sulfones such as sulfolane; or halogenated hydrocarbons such as methylene chloride, chloroform, carbon tetrachloride, trichloroethane, chlorobenzene, trichlorofluoromethane, dichlorodifluoromethane, 1,2-dichloro-1,1,2,2-tetrafluoroethane, chlorotrifluoromethane or hydrogen fluoride. If hydrogen fluoride itself is used as solvent, the excess thereof may be very much greater.

The process of the present invention is preferably carried out under normal pressure. However, in isolated cases it may prove necessary to carry out the reaction under vacuum or under excess pressure. Reaction pressure can in general be held in the range from 0.1 to 20 bar.

In general, reaction times ranging from several minutes to 24 hours are necessary to convert the starting material of formula II fully into the compound of formula I by the process of the present invention. Reaction conditions will preferably be chosen such that the reaction times are from 0.5 to 4 hours.

A preferred process of the present invention for the preparation of α,α-difluoroalkyl phenyl ethers of formula I comprises carrying out the reaction in the presence of 0.1 to 50 mol% of antimony(V) halide, at a temperature in the range from $-20°$ C. to $+100°$ C. and under a pressure in the range from 0.1 to 20 bar.

A particularly preferred embodiment comprises carrying out the reaction in the presence of 1 to 20 mol% of antimony(V) chloride, at a temperature in the range from $-10°$ C. to $+20°$ C. and under normal pressure, in liquid hydrogen fluoride.

The process (II→I) of the present invention is particularly suitable for the preparation of α,α-difluoroalkyl phenyl ethers of the narrower formula Ia

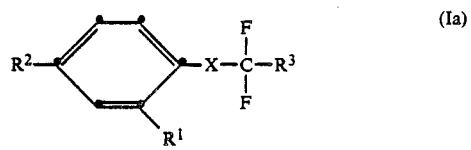

wherein
$R^1$ is hydrogen, halogen, nitro, amino, $—SO_2—R^4$, $—S—R^5$ or $—SO—R^6$,
$R^2$ is hydrogen, halogen or nitro,
$R^3$ is $C_1-C_3$perfluoroalkyl,
X is oxygen or sulfur,
$R^4$ is hydroxy, amino, phenyl, benzyl, $C_1-C_4$alkyl or halogen, preferably fluorine or chlorine and
$R^5$ and $R^6$ are $C_1-C_4$alkyl or benzyl.

Among these compounds of formula Ia, it is preferred to prepare by the novel process of the present invention those compounds, wherein $R^1$ is $—SO_2NH_2$, hydrogen or chlorine, $R^2$ is hydrogen or chlorine, $R^3$ is $C_1-C_3$perfluoroalkyl and X is oxygen or sulfur. Among these compounds, special mention is made of those wherein one of $R^1$ and $R^2$ is chlorine and the other is hydrogen or chlorine.

Preferred individual compounds of formula I are, besides 2-perfluoroethoxyphenylsulfonamide, especially 2,4-dichloroperfluoroethoxybenzene, 2-perfluoroethoxychlorobenzene and 4-perfluoroethoxychlorobenzene.

These particularly preferred compounds of formula I selected from the group consisting of 2-perfluoroethoxyphenylsulfonamide, 2,4-dichloroperfluoroethoxybenzene, 2-perfluoroethoxychlorobenzene or 4-perfluoroethoxychlorobenzene are preferably prepared by fluorinating 2-(1,1-dichloro-2,2,2-trifluoroethoxy)phenylsulfonamide, 1-(1,1-dichloro-2,2,2-trifluoroethoxy)-2,4-dichlorobenzene, 2-(1,1-dichloro-2,2,2-trifluoroethoxy)chlorobenzene or 4-(1,1-dichloro-2,2,2-trifluoroethoxy)chlorobenzene, in the presence of 5 to 20 mol% of antimony(V) chloride, at a temperature in the range from $-10°$ C. to $+10°$ C. and under normal pressure, in liquid hydrogen fluoride.

In one variant, the process (II→I) of the present invention may also be carried out in two steps by first converting the compound of formula II with hydrogen fluoride into the intermediate of formula III

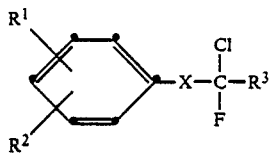

(III)

wherein $R^1$, $R^2$, $R^3$ and X are as defined for formula I in claim 1, in the presence of 0.1 to 5 mol% of antimony(V) halide, and reacting said intermediate with hydrogen fluoride, in the presence of 1 to 20 mol% of antimony(V) halide, to give the compound of formula I.

In said two-step process variant, it is preferred to carry out the reaction of the compound of formula II to give the compound of formula III at a temperature in the range from $-20°$ C. to $0°$ C. and to carry out the further reaction of the intermediate at a temperature in the range from $0°$ C. to $+100°$ C.

When carrying out said variant, the intermediates of formula III may either be isolated or used direct, without isolation, for further reaction in the second step. The reaction conditions for the two-step variant, such as pressure, temperature, solvent and concentration of catalyst, are selected under the conditions of the single-step process of the present invention, with the indicated restrictions.

If for operational reasons a two-step process is desired, it is necessary to carry out the first step with a low concentration of catalyst and/or at low temperature. In order to carry out the second step, it is convenient to increase the concentration of catalyst and/or the temperature. The concentrations of catalyst and reaction temperatures for both steps may vary according to the constitution and substitution of the phenyl nucleus of the starting material of formula II and have to be adapted to the respective reactivity of the molecule of the starting material and of the intermediate.

The fluorination process of the present invention may be carried out according to conventional chemical process technology in batchwise or continuously operating reactors. The reaction medium is either liquid or gaseous, depending on the temperature and pressure of the reaction.

The starting materials of formula II are known or they can be prepared by known methods. Preferably, the α,α-dichloroalkyl phenyl ether derivatives of formula II are prepared from corresponding phenyl alkanecarboxylates by treatment with customary chlorinating agents such as phosphorus pentachloride, phosphorus trichloride, chlorine, phosphorus oxychloride or thionyl chloride. The compounds of formula II can also be prepared by α-chlorination of corresponding phenylalkyl ethers with gaseous chlorine.

The first step of the above process for the preparation of compounds of formula I serves at the same time as an independent process for the preparation of α-chloro-α-fluoroalkyl phenyl ether derivatives of formula III. This process constitutes a further object of the present invention.

The process of the present invention for the preparation of an α-chloro-α-fluoroalkyl phenyl ether derivative of formula III

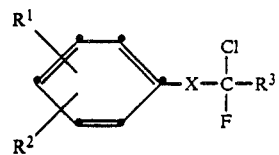

(III)

wherein
$R^1$ is hydrogen, halogen, amino, nitro, $-SO_2-R^4$, $-SO-R^5$, $-SO-R^6$ or $-S-S-R^7$,
$R^2$ is hydrogen, halogen, nitro, hydroxy or $-SO_2-R^8$,
$R^3$ is $C_1-C_5$haloalkyl,
X is oxygen, sulfur, $-SO-$ or $-SO_2-$,
$R^4$ is hydroxy, halogen, amino, benzyl, phenyl, $C_1-C_4$alkyl, $-N=C=O$, $-NH-CO-Cl$, $-NH-CO-Br$, $-NR^9R^{10}$ or $-NH-CO-NR^{11}R^{12}$,
$R^5$ and $R^6$ are $C_1-C_4$alkyl, phenyl or benzyl,
$R^7$ is $C_1-C_4$alkyl, phenyl or benzyl,
$R^8$ is hydroxy or halogen,
$R^9$ and $R^{10}$ are each independently of the other $C_1-C_4$alkyl or benzyl and
$R^{11}$ and $R^{12}$ are each independently of the other hydrogen, $C_1-C_4$alkyl, phenyl or an aromatic heterocycle,
comprises fluorinating a compound of formula II

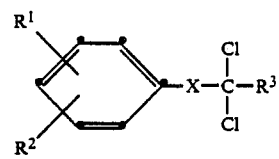

(II)

wherein $R^1$, $R^2$, $R^3$ and X are as defined for formula III, with hydrogen fluoride, in the presence of a catalytic amount of an antimony(V) compound.

The individual substituents as defined for formula III are the same as the individual substituents already mentioned for formula I.

The intermediates of formula III are either themselves herbicidal sulfonylureas or they can be converted into herbicidal sulfonylureas by one or more reaction steps which are known per se. Accordingly, by continued fluorination the α-chlorine atom of the compound of formula III can also be replaced by fluorine, affording a herbicidal sulfonylurea derivative of formula I. Compounds of formula III, wherein $R^1$ is the radical $-SO_2-NH-CO-NR^{11}R^{12}$, where $R^{11}$ or $R^{12}$ is a pyrimidine or triazine ring, are likewise herbicidal sulfonylureas.

If $R^1$ is another sulfonic acid derivative, e.g. the free acid, an acid amide, an acid halide, an isocyanatosulfonyl radical or a carbamoylsulfonyl radical, then said derivatives can be converted into sulfonylurea derivatives by reaction methods which are known per se. Various methods are also known to the skilled person enabling him to convert compounds of formula III, wherein $R^1$ is hydrogen, halogen, amino, nitro, $-S-R^5$, $-SO-R^6$ or $-S-S-R^7$, into phenylsulfonic acid derivatives and subsequently into herbicidal sulfonylureas.

The fluorination catalyst used for carrying out the process of the present invention for the preparation of compounds of formula III is an antimony compound in which the antimony atom is present in oxidation state V. The use of this catalyst makes it possible at the same time to employ the relatively easily accessible hydrogen fluoride as fluorinating agent and to lower the reaction temperature. The lowering of the reaction temperature and the concomitant decrease in pressure result in a reduction of operating costs of the reactor. In favourable circumstances, the reaction may be carried out under normal pressure or under slight vacuum.

To carry out said monofluorination process, lower concentrations of catalyst and/or lower reaction temperatures are applied than for the difluorination of the same starting material. Depending on the reactivity of the starting material of formula II, the reaction parameters to be applied may overlap. For example at a particular temperature and at a particular concentration of catalyst, an inert compound of formula II can be monofluorinated to give a compound of formula III, while under the same reaction conditions a more reactive compound is difluorinated to give a compound of formula I. Suitable reaction conditions are specially chosen in each case with regard to the desired product of formula I or III.

It is preferred to use an antimony(V) halide as fluorination catalyst for the reaction (II→III). Antimony pentachloride is particularly preferred on account of its ready accessibility.

Catalyst systems which form antimony(V) compounds as intermediates are also suitable. Examples of such catalyst systems are mixtures of antimony trichloride and a halogen. To be specifically mentioned here is the mixture of antimony trichloride and bromine.

In the reaction (II→III), the proportion of catalyst in the reaction mixture can vary within wide limits. The reaction of the present invention can be carried out using 0.1 to 50 mol% of antimony(V) compound, based on the amount of starting material of formula II employed. Reaction rates suitable for industrial application in a large-scale reactor are attained by using as catalyst 1 to 20 mol%, preferably 5 to 20 mol%, of antimony(V) halide.

By using the novel fluorination catalyst, it is possible to carry out the reaction (II→III) under mild reaction conditions, i.e. at relatively low reaction temperature. Accordingly, the reaction temperature is generally in the range from −20° C. to +100° C. It is preferred to keep the reaction temperature in the range from −10° C. to +20° C. The hydrogen fluoride employed as fluorinating agent is used in at least equivalent amount. Generally, an excess of hydrogen fluoride of 0.5 to 2 mol is used. The reaction may be carried out without a solvent or in the presence of an inert solvent. Suitable inert solvents are: amides such as dimethylformamide or N-methylpyrrolidone; aromatic hydrocarbons such as benzene, toluene or xylene; sulfoxides such as dimethylsulfoxide; sulfones such as sulfolane; or halogenated hydrocarbons such as methylene chloride, chloroform, carbon tetrachloride, trichloroethane, chlorobenzene, trichlorofluoromethane, dichlorodifluoromethane, 1,2-dichloro-1,1,2,2-tetrafluoroethane, chlorotrifluoromethane or hydrogen fluoride. If hydrogen fluoride itself is used as solvent, the excess thereof may be very much greater. The process (II→III) of the present invention is preferably carried out under normal pressure. However, in isolated cases it may prove necessary to carry out the reaction under vacuum or under excess pressure. Reaction pressure can in general be held in the range from 0.1 to 20 bar.

In general, reaction times ranging from several minutes to 24 hours are necessary to convert the starting material of formula II fully into the compound of formula III by the process of the present invention. Reaction conditions will preferably be chosen such that the reaction times are from 0.5 to 4 hours.

A preferred process of the present invention for the preparation of α-chloro-α-fluoralkyl phenyl ethers of formula III comprises carrying out the reaction in the presence of 0.1 to 50 mol% of antimony(V) halide, at a temperature in the range from −20° C. to +100° C. and under a pressure in the range from 0.1 to 20 bar. A particularly preferred embodiment comprises carrying out the reaction in the presence of 1 to 20 mol% of antimony(V) chloride, at a temperature in the range from −10° C. to +20° C. and under normal pressure, in liquid hydrogen fluoride.

The process of the present invention is particularly suitable for the preparation of α-chloro-α-fluoroalkyl phenyl ethers of the narrower formula IIIa

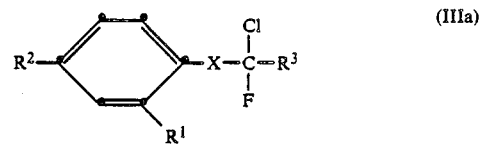

wherein
R$^1$ is hydrogen, halogen, nitro, amino, —SO$_2$—R$^4$, —S—R$^5$ or —SO—R$^6$,
R$^2$ is hydrogen, halogen or nitro,
R$^3$ is C$_1$–C$_3$perfluoroalkyl,
X is oxygen or sulfur,
R$^4$ is hydroxy, amino, phenyl, benzyl, C$_1$–C$_4$alkyl or halogen, preferably fluorine or chlorine, and
R$^5$ and R$^6$ are C$_1$–C$_4$alkyl or benzyl.

Among these intermediates, it is preferred to prepare by the novel process of the present invention those compounds, wherein R$^1$ is —SO$_2$NH$_2$, hydrogen or chlorine, R$^2$ is hydrogen or chlorine, R$^3$ is C$_1$–C$_3$perfluoroalkyl and X is oxygen or sulfur. Among these compounds, special mention is made of those wherein one of R$^1$ and R$^2$ is chlorine and the other is hydrogen or chlorine.

Preferred individual compounds of formula III are, besides 2-(1-chloro-1,2,2,2-tetrafluoroethoxy)phenylsulfonamide, especially 2,4-dichloro-(1-chloro-1,2,2,2-tetrafluoroethoxy)benzene, 2-(1-chloro-1,2,2,2-tetrafluoroethoxy)chlorobenzene and 4-(1-chloro-1,2,2,2-tetrafluoroethoxy)chlorobenzene.

These particularly preferred compounds of formula III selected from the group consisting of 2-(1-chloro-1,2,2,2-tetrafluoroethoxy)phenylsulfonamide, 2,4-dichloro-(1-chloro-1,2,2,2-tetrafluoroethoxy)benzene, 2-(1-chloro-1,2,2,2-tetrafluoroethoxy)chlorobenzene or 4-(1-chloro-1,2,2,2-tetrafluoroethoxy)chlorobenzene are preferably prepared by fluorinating 2-(1,1-dichloro-2,2,2-trifluoroethoxy)phenylsulfonamide, 1-(1,1-dichloro-2,2,2-trifluoroethoxy)-2,4-dichlorobenzene, 2-(1,1-dichloro-2,2,2-trifluoroethoxy)chlorobenzene or 4-(1,1-dichloro-2,2,2-trifluoroethoxy)chlorobenzene, in the presence of 1 to 5 mol% of antimony(V) chloride, at a temperature in the range from −10° C. to 0° C. and under normal pressure, in liquid hydrogen fluoride.

The fluorination process (II→III) of the present invention may be carried out according to conventional chemical process technology in batchwise or continuously operating reactors. The reaction medium is either liquid or gaseous, depending on the temperature and pressure of the reaction.

Some of the intermediates of formula III prepared by the novel process are novel and thus constitute a further object of the present invention. These novel compounds are of the subformulae IIIb

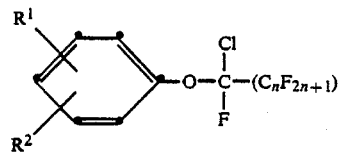
(IIIb)

wherein $R^1$ and $R^2$ are as defined for formula III and n is a value from 1 to 5, and IIIc

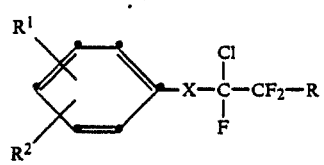
(IIIc)

wherein $R^1$ and $R^2$ are as defined for formula III, X is sulfur, SO or $SO_2$ and R is fluorine or $C_1$-$C_4$perhaloalkyl.

The following Tables 1 to 3 contain examples of starting materials, intermediates and final products of formulae I, II and III which may be reacted or obtained by the process of the present invention.

TABLE 1

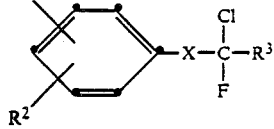

| Compound | $R^1$ | $R^2$ | $R^3$ | X | Physical data |
|---|---|---|---|---|---|
| 1.1 | H | H | $CF_3$ | O | b.p. 183° C. |
| 1.2 | 4-Cl | H | $CF_3$ | O | b.p. 218° C. |
| 1.3 | 2-Cl | H | $CF_3$ | O | b.p. 222° C. |
| 1.4 | 4-Cl | 2-$NO_2$ | $CF_3$ | O | |
| 1.5 | 2-Cl | 4-Cl | $CF_3$ | O | |
| 1.6 | 2-$NH_2$ | H | $CF_3$ | O | |
| 1.7 | 2-$SO_2$—$NH_2$ | H | $CF_3$ | O | |
| 1.8 | 2-$SO_2$—OH | H | $CF_3$ | O | |
| 1.9 | 2-$SO_2$—Cl | H | $CF_3$ | O | |
| 1.10 | 2-$SO_2$—OH | H | $C_2F_5$ | O | |
| 1.11 | 2-$SO_2$—$NH_2$ | H | $CF_3$ | S | |
| 1.12 | 2-$SO_2$—$NH_2$ | H | $CCl_3$ | O | |
| 1.13 | 2-$SO_2$—Cl | H | $CCl_3$ | O | |
| 1.14 | 2-$NO_2$ | H | $CF_3$ | O | |
| 1.15 | 2-$NO_2$ | H | $CHF_2$ | O | |
| 1.16 | 2-$NH_2$ | H | $CHF_2$ | O | |
| 1.17 | 2-$NO_2$ | H | $CF_3$ | S | |
| 1.18 | 2-$NO_2$ | H | $C_3H_7$—n | O | |
| 1.19 | 2-$NH_2$ | H | $CF_3$ | S | |
| 1.20 | 4-Cl | 3-$NO_2$ | $CF_3$ | O | |
| 1.21 | 4-Cl | 3-Cl | $CF_3$ | O | |
| 1.22 | 4-Cl | 3-$NO_2$ | $CF_3$ | S | |
| 1.23 | 4-Cl | 2-$NO_2$ | $CF_3$ | S | |
| 1.24 | 2-Cl | H | $CF_3$ | S | |
| 1.25 | 2-S—S—$C_6H_5$ | H | $CF_3$ | O | |
| 1.26 | 2-S—$CH_2$—$C_6H_5$ | H | $CF_3$ | O | |
| 1.27 | H | H | $CF_3$ | S | b.p. 218° C. |
| 1.28 | 2-$SO_2$—Cl | 5-$SO_2$—Cl | $CF_3$ | O | |

TABLE 2

| Compound | $R^1$ | $R^2$ | $R^3$ | X | Physical data |
|---|---|---|---|---|---|
| 2.1 | H | H | $CF_3$ | O | b.p. 150° C. |
| 2.2 | 4-Cl | H | $CF_3$ | O | b.p. 181° C. |
| 2.3 | 2-Cl | H | $CF_3$ | O | |
| 2.4 | 4-Cl | 2-$NO_2$ | $CF_3$ | O | |
| 2.5 | 2-Cl | 4-Cl | $CF_3$ | O | |
| 2.6 | 2-$NH_2$ | H | $CF_3$ | O | |
| 2.7 | 2-$SO_2$—$NH_2$ | H | $CF_3$ | O | |
| 2.8 | 2-$SO_2$—OH | H | $CF_3$ | O | |
| 2.9 | 2-$SO_2$—Cl | H | $CF_3$ | O | |
| 2.10 | 2-$SO_2$—OH | H | $C_2F_5$ | O | |
| 2.11 | 2-$SO_2$—$NH_2$ | H | $CF_3$ | S | |
| 2.12 | 2-$SO_2$—$NH_2$ | H | $CCl_3$ | O | |
| 2.13 | 2-$SO_2$—Cl | H | $CCl_3$ | O | |
| 2.14 | 2-$NO_2$ | H | $CF_3$ | O | |
| 2.15 | 2-$NO_2$ | H | $CHF_2$ | O | |
| 2.16 | 2-$NH_2$ | H | $CHF_2$ | O | |
| 2.17 | 2-$NO_2$ | H | $CF_3$ | S | |
| 2.18 | 2-$NO_2$ | H | $C_3H_7$—n | O | |
| 2.19 | 2-$NH_2$ | H | $CF_3$ | S | |
| 2.20 | 4-Cl | 3-$NO_2$ | $CF_3$ | O | |
| 2.21 | 4-Cl | 3-Cl | $CF_3$ | O | |
| 2.22 | 4-Cl | 3-$NO_2$ | $CF_3$ | S | |
| 2.23 | 4-Cl | 2-$NO_2$ | $CF_3$ | S | |
| 2.24 | 2-Cl | H | $CF_3$ | S | |
| 2.25 | 2-S—S—$C_6H_5$ | H | $CF_3$ | O | |
| 2.26 | 2-S—$CH_2$—$C_6H_5$ | H | $CF_3$ | O | |
| 2.27 | H | H | $CF_3$ | S | b.p. 178–179° C. |
| 2.28 | 2-$SO_2$—Cl | 5-$SO_2$—Cl | $CF_3$ | O | |

TABLE 3

| Compound | $R^1$ | $R^2$ | $R^3$ | X | Physical data |
|---|---|---|---|---|---|
| 3.1 | H | H | $CF_3$ | O | b.p. 118° C. |
| 3.2 | 4-Cl | H | $CF_3$ | O | b.p. 160° C. |
| 3.3 | 2-Cl | H | $CF_3$ | O | b.p. 154° C. |
| 3.4 | 4-Cl | 2-$NO_2$ | $CF_3$ | O | |
| 3.5 | 2-Cl | 4-Cl | $CF_3$ | O | |
| 3.6 | 2-$NH_2$ | H | $CF_3$ | O | b.p. 175° C. |
| 3.7 | 2-$SO_2$—$NH_2$ | H | $CF_3$ | O | m.p. 148° C. |
| 3.8 | 2-$SO_2$—OH | H | $CF_3$ | O | |
| 3.9 | 2-$SO_2$—Cl | H | $CF_3$ | O | |
| 3.10 | 2-$SO_2$—OH | H | $C_2F_5$ | O | |
| 3.11 | 2-$SO_2$—$NH_2$ | H | $CF_3$ | S | |
| 3.12 | 2-$SO_2$—$NH_2$ | H | $CCl_3$ | O | |
| 3.13 | 2-$SO_2$—Cl | H | $CCl_3$ | O | |
| 3.14 | 2-$NO_2$ | H | $CF_3$ | O | |
| 3.15 | 2-$NO_2$ | H | $CHF_2$ | O | |
| 3.16 | 2-$NH_2$ | H | $CHF_2$ | O | |
| 3.17 | 2-$NO_2$ | H | $CF_3$ | S | |
| 3.18 | 2-$NO_2$ | H | $C_3H_7$—n | O | |
| 3.19 | 2-$NH_2$ | H | $CF_3$ | S | |
| 3.20 | 4-Cl | 3-$NO_2$ | $CF_3$ | O | |
| 3.21 | 4-Cl | 3-Cl | $CF_3$ | O | |
| 3.22 | 4-Cl | 3-$NO_2$ | $CF_3$ | S | |
| 3.23 | 4-Cl | 2-$NO_2$ | $CF_3$ | S | |
| 3.24 | 2-Cl | H | $CF_3$ | S | |
| 3.25 | 2-S—S—$C_6H_5$ | H | $CF_3$ | O | |
| 3.26 | 2-S—$CH_2$—$C_6H_5$ | H | $CF_3$ | O | |
| 3.27 | H | H | $CF_3$ | S | b.p. 148° C. |

TABLE 3-continued

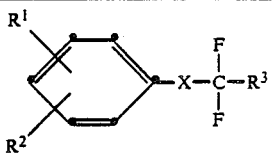

| Compound | R¹ | R² | R³ | X | Physical data |
|---|---|---|---|---|---|
| 3.28 | 2-SO₂—Cl | 5-SO₂—Cl | CF₃ | O | |

The following Examples serve to illustrate the invention in more detail.

EXAMPLE 1

4-Perfluoroethoxychlorobenzene

A 300 ml Monel reactor equipped with stirrer, thermometer and reflux condenser is charged with 55.9 g (0.2 mol) of 4-(1,1-dichloro-2,2,2-trifluoroethoxy)-chlorobenzene and 6.0 g (0.02 mol; corresponding to 10 mol%) of antimony pentachloride. 100 g of hydrogen fluoride are introduced at a temperature in the range from −10° C. to 0° C. The resultant hydrogen chloride is removed from the apparatus through the reflux condenser. After 2½ hours, a further 6.0 g (0.02 mol) of antimony pentachloride are added to the reaction mixture. After a total reaction time of 5 hours, the hydrogen fluoride is removed by distillation, the residue is dissolved in 250 ml of methylene chloride and 50 g of potassium fluoride are added to the solution. The solution is then separated by distillation, affording 45.1 g (91.5% of theory) of 4-perfluoroethoxychlorobenzene. Boiling point 151° C., $n_D^{25} = 1.4080$.

EXAMPLE 2

4-Perfluoroethoxychlorobenzene

A 500 ml polytetrafluoroethylene reactor equipped with stirrer, thermometer and reflux condenser is charged with 55.9 g (0.2 mol) of 4-(1,1-dichloro-2,2,2-trifluoroethoxy)chlorobenzene in 100 ml of hydrogen fluoride. 3.0 g (0.01 mol; corresponding to 5 mol%) of antimony pentachloride are added at a temperature of +10° C. The resultant hydrogen chloride is removed from the reactor through the reflux condenser. After 2 hours at +10° C., the evolution of hydrogen chloride ceases. Excess hydrogen fluoride is removed by distillation, the residue is dissolved in 200 ml of methylene chloride and the solution is extracted with water. The organic phase is separated by distillation, affording 44.9 g (90.8% of theory) of 4-perfluoroethoxychlorobenzene. Boiling point 151° C.

EXAMPLE 3

Perfluoroethoxybenzene

A 500 ml polytetrafluoroethylene reactor equipped with stirrer, thermometer and reflux condenser is charged with 49.0 g (0.2 mol) of 1,1-dichloro-2,2,2-trifluoroethoxybenzene in 100 ml of hydrogen fluoride. 7.0 g (corresponding to 12 mol%) of antimony pentachloride are added at a temperature in the range from −5° C. to 0° C. The resultant hydrogen chloride is removed from the reactor through the reflux condenser. Afters 5 hours at 0° C., the evolution of hydrogen chloride ceases. Excess hydrogen fluoride is removed by distillation, the residue is dissolved in 250 ml of methylene chloride and the solution is extracted with water. The organic phase is separated by distillation, affording 27.4 g (64.5% of theory) of perfluoroethoxybenzene.

Boiling point 118° C., $n_D^{25} = 1.3790$.

EXAMPLE 4

2-Perfluoroethoxychlorobenzene

A 2 l polytetrafluoroethylene reactor equipped with stirrer, thermometer and reflux condenser is charged with 279.5 g (1 mol) of 2-(1,1-dichloro-2,2,2-trifluoroethoxy)chlorobenzene in 500 ml of hydrogen fluoride. 70.0 g (corresponding to 25 mol%) of antimony pentachloride is added at a temperature in the range from −5° C. to 0° C. The resultant hydrogen chloride is removed from the reactor through the reflux condenser. After 24 hours at 0° C., the evolution of hydrogen chloride ceases. Excess hydrogen fluoride is removed by distillation, the residue is dissolved in 1.5 l of methylene chloride and the solution is extracted with water. The organic phase is separated by distillation, affording 175.5 g (71.3% of theory) of 2-perfluoroethoxychlorobenzene. Boiling point 154° C., $n_D^{25} = 1.4106$.

EXAMPLE 5

4-Perfluoroethoxychlorobenzene

A 500 ml polytetrafluoroethylene reactor equipped with stirrer, thermometer and reflux condenser is charged with 52.6 g (0.2 mol) of 4-(1-chloro-1,2,2,2-tetrafluoroethoxy)chlorobenzene in 100 ml of hydrogen fluoride. 6.0 g (0.02 mol; corresponding to 10 mol%) of antimony pentachloride are added at a temperature in the range from −5° C. to 0° C. The resultant hydrogen chloride is removed from the reactor through the reflux condenser. After 4 hours at a temperature in the range from 0° C. to +5° C., the evolution of hydrogen chloride ceases. Excess hydrogen fluoride is removed by distillation, the residue is dissolved in 200 ml of methylene chloride and the solution is extracted with water. The organic phase is separated by distillation, affording 43.7 g (89.5% of theory) of 4-perfluoroethoxychlorobenzene. Boiling point 151° C.

EXAMPLE 6

4-Perfluoroethoxychlorobenzene

A 500 ml polytetrafluoroethylene reactor equipped with stirrer, thermometer and reflux condenser is charged with 55.9 g (0.2 mol) of 4-(1,1-dichloro-2,2,2-trifluoroethoxy)chlorobenzene in 16 g of hydrogen fluoride. 6.0 g (0.02 mol; corresponding to 10 mol%) of antimony pentachloride are added at a temperature of +10° C. The resultant hydrogen chloride is removed from the reactor through the reflux condenser. After 1½ hours at +10° C., the evolution of hydrogen chloride ceases. The residue is dissolved in 200 ml of methylene chloride and the solution is extracted with water. The organic phase is separated by distillation, affording 44.7 g (90.4% of theory) of 4-perfluoroethoxychlorobenzene. Boiling point 151° C.

EXAMPLE 7

4-(1-Chloro-1,2,2,2-tetrafluoroethoxy)chlorobenzene

A 500 ml polytetrafluoroethylene reactor equipped with stirrer, thermometer and reflux condenser is charged with 55.9 g (0.2 mol) of 4-(1,1-dichloro-2,2,2- trifluoroethoxy)chlorobenzene in 100 ml of hydrogen fluoride. 3.0 g (0.01 mol; corresponding to 5 mol%) of antimony pentachloride are added at a temperature in the range from −5° C. to 0° C. The resultant hydrogen chloride is removed from the reactor through the reflux condenser. After 20 minutes at 0° C., the evolution of hydrogen chloride ceases. Excess hydrogen fluoride is removed by distillation, the residue is dissolved in 200 ml of methylene chloride and the solution is extracted with water. The organic phase is separated by distillation, affording 47.3 g (89.8% of theory) of 4-(1-chloro-1,2,2,2-tetrafluoroethoxy)chlorobenzene. Boiling point 181° C., $n_D^{25}=1.4362$.

EXAMPLE 8

4-Perfluoroethoxyfluorobenzene

A 500 ml polytetrafluoroethylene reactor equipped with stirrer, thermometer and reflux condenser is charged with 17.0 g (0.0646 mol) of 4-(1,1-dichloro-2,2,2-trifluoroethoxy)fluorobenzene and 35 g of hydrogen fluoride. 2.0 g ($6.7.10^{-3}$ mol; corresponding to 10 mol%) of antimony pentachloride are added at a temperature of +10° C. The resultant hydrogen chloride is removed from the reactor through the reflux condenser. After 1 hour, a further 1.0 g of antimony pentachloride is added to the reaction mixture. After a total reaction time of 4 hours, the hydrogen fluoride is removed by distillation, the residue is dissolved in 150 ml of methylene chloride and the solution is extracted with water. The organic phase is separated by distillation, affording 4-perfluoroethoxyfluorobenzene. Boiling point 121° C., $n_D^{26}=1.3710$.

EXAMPLE 9

1-Chloro-1,2,2,2-tetrafluoroethylthiobenzene

A 500 ml polytetrafluoroethylene reactor equipped with stirrer, thermometer and reflux condenser is charged with 24.7 g (0.094 mol) of 1,1-dichloro-2,2,2-trifluoroethylthiobenzene which are subsequently condensed with 50 g of hydrogen fluoride. 4.2 g (0.014 mol; corresponding to 15 mol%) of antimony pentachloride are added at a temperature of 20° C. The resultant hydrogen chloride is removed from the reactor through the reflux condenser. After 3 hours a further 1.4 g (5 mol%) and after 4 hours a further 2.8 g (10 mol%) of antimony pentachloride are added. After a total reaction time of 5 hours, the hydrogen fluoride is removed by distillation, the residue is dissolved in 150 ml of methylene chloride and the solution is extracted with water. The solution is separated by distillation, affording 1-chloro-1,2,2,2-tetrafluoroethylthiobenzene. Boiling point 178°–179° C., $n_D^{20}=1.4732$.

What is claimed is:

1. A process for the preparation of an α,α-difluoroalkyl phenyl ether of formula I

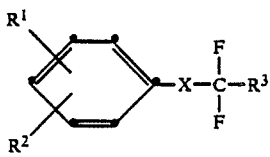

(I)

wherein $R^1$ is hydrogen, halogen, amino, nitro, $-SO_2-R^4$, $-S-R^5$, $-SO-R^6$ or $-S-S-R^7$, $R^2$ is hydrogen, halogen, nitro, hydroxy or $-SO_2-R^8$, $R^3$ is $C_1-C_5$haloalkyl, X is oxygen, sulfur, $-SO-$ or $-SO_2-$, $R^4$ is hydroxy, halogen, amino, $-N=C=O$, $-NH-CO-Cl$, $-NH-CO-Br$, $-NR^9R^{10}$, benzyl, phenyl, $C_1-C_4$alkyl or $-NH-CO-NR^{11}R^{12}$, $R^5$ and $R^6$ are $C_1-C_4$alkyl, phenyl or benzyl, $R^7$ is $C_1-C_4$alkyl, phenyl or benzyl, $R^8$ is hydroxy or halogen, $R^9$ and $R^{10}$ are each independently of the other $C_1-C_4$alkyl or benzyl and $R^{11}$ and $R^{12}$ are each independently of the other hydrogen, $C_1-C_4$-alkyl, phenyl or an aromatic heterocycle which process comprises fluorinating a compound of formula II

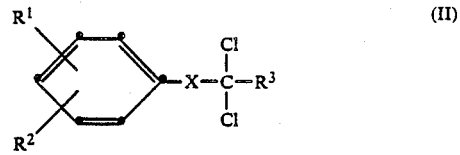

(II)

wherein $R^1$, $R^2$, $R^3$ and X are as defined for formula I, with hydrogen fluoride, in the presence of a catalytic amount of an antimony(V) compound.

2. A process according to claim 1, wherein the fluorination catalyst is an antimony(V) halide.

3. A process according to claim 2, wherein the fluorination catalyst is antimony pentachloride.

4. A process according to claim 2, wherein the antimony (V) halide fluorination catalyst is formed in-situ from a mixture of antimony trichloride and a halogen.

5. A process according to claim 1, which comprises the use of 0.1 to 50 mol% of antimony(V) compound, based on the amount of the starting material of formula II employed.

6. A process according to claim 5, which comprises the use of 1 to 20 mol% of antimony(V) halide.

7. A process according to claim 1, which comprises carrying out the reaction at a temperature in the range from −20° C. to +100° C.

8. A process according to claim 1, wlhich comprises carrying out the reaction at a temperature in the range from −10° C. to +20° C.

9. A process according to claim 1, which comprises carrying out the reaction with an excess of hydrogen fluoride.

10. A process according to claim 1, which comprises carrying out the reaction under a pressure in the range from 0.1 to 20 bar.

11. A process according to claim 1, which comprises preparing a compound of formula Ia

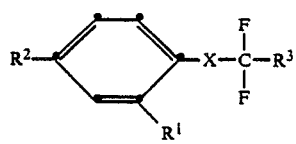

(Ia)

wherein $R^1$ is hydrogen, halogen, nitro, amino, $-SO_2-R^4$, $-S-R^5$ or $-SO-R^6$, $R^2$ is hydrogen, halogen or nitro, $R^3$ is $C_1-C_3$perfluoroalkyl, X is oxygen or sulfur, $R^4$ is hydroxy, amino, phenyl, benzyl, $C_1$–$C_4$alkyl or halogen, preferably fluorine or chlorine and $R^5$ and $R^6$ are $C_1$–$C_4$alkyl or benzyl.

12. A process according to claim 11, wherein $R^1$ is —$SO_2$—$NH_2$, hydrogen or chlorine, $R^2$ is hydrogen or chlorine, $R^3$ is $C_1$–$C_3$perfluoroalkyl and X is oxygen or sulfur.

13. A process according to claim 12, wherein one of $R^1$ and $R^2$ is chlorine and the other is hydrogen or chlorine.

14. A process according to claim 1, which comprises preparing the compound 2-perfluoroethoxyphenylsulfonamide.

15. A process according to claim 12, which comprises preparing a compound selected from the group consisting of 2,4-dichloroperfluoroethoxybenzene, 2-perfluoroethoxychlorobenzene or 4-perfluoroethoxychlorobenzene.

16. A process according to claim 1, which comprises carrying out the reaction in the presence of 0.1 to 50 mol% of antimony(V) halide, at a temperature in the range from −20° C. to +100° C. and under a pressure in the range from 0.1 to 20 bar.

17. A process according to claim 1, which comprises carrying out the reaction in the presence of 1 to 20 mol% of antimony(V) chloride, at a temperature in the range from −10° C. to +20° C. and under normal pressure, in liquid hydrogen fluoride.

18. A process according to claim 1 for the preparation of a compound selected from the group consisting of 2-perfluoroethoxyphenylsulfonamide, 2,4-dichloroperfluoroethoxybenzene, 2-perfluoroethoxychlorobenzene or 4-perfluoroethoxychlorobenzene, which process comprises fluorinating 2-(1,1-dichloro-2,2,2-trifluoroethoxy)phenylsulfonamide, 1-(1,1-dichloro-2,2,2-trifluoroethoxy)-2,4-dichlorobenzene, 2-(1,1-dichloro-2,2,2-trifluoroethoxy)chlorobenzene or 4-(1,1-dichloro-2,2,2-trifluoroethoxy)chlorobenzene, in the presence of 5 to 20 mol% of antimony(V) chloride, at a temperature in the range from −10° C. to +10° C. and under normal pressure, in liquid hydrogen fluoride.

19. A process according to claim 1, which comprises carrying out the process in 2 steps, by first converting the compound of formula II with hydrogen fluoride into the intermediate of the formula III

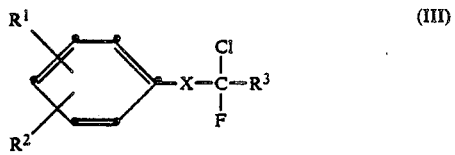

(III)

wherein $R^1$, $R^2$, $R^3$ and X are as defined for formula I as claimed in claim 1, in the presence of 0.1 to 5 mol% of antimony(V) halide, and reacting said intermediate with hydrogen fluoride, in the presence of 1 to 20 mol% of antimony(V) halide, to give the compound of formula I.

20. A process according to claim 19, which comprises carrying out the reaction of the compound of formula II to give the compound of formula III at a temperature in the range from −20° C. to 0° C. and carrying out the further reaction of the intermediate of formula III at a temperature in the range from 0° C. to +100° C.

21. A process for the preparation of a compound of formula III

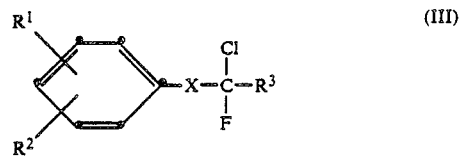

(III)

wherein $R^1$ is hydrogen, halogen, amino, nitro, —SO—$R^4$, —S—$R^5$, —SO—$R^6$ or —S—S—$R^7$, $R^2$ is hydrogen, halogen, nitro, hydroxy or —$SO_2$—$R^8$, $R^3$ is $C_1$–$C_5$haloalkyl, X is oxygen, sulfur, —SO— or —$SO_2$—, $R^4$ is hydroxy, halogen, amino, benzyl, phenyl, $C_1$–$C_4$alkyl, —N=C=O, —NH—CO—Cl, —NH—CO—Br, —$NR^9R^{10}$ or —NH—CO—$NR^{11}R^{12}$, $R^5$ and $R^6$ are $C_1$–$C_4$alkyl, phenyl or benzyl, $R^7$ is $C_1$–$C_4$alkyl, phenyl or benzyl, $R^8$ is hydroxy or halogen, $R^9$ and $R^{10}$ are each independently of the other $C_1$–$C_4$alkyl or benzyl and $R^{11}$ and $R^{12}$ are each independently of the other hydrogen, $C_1$–$C_4$alkyl, phenyl or an aromatic heterocycle, which process comprises fluorinating a compound of formula II

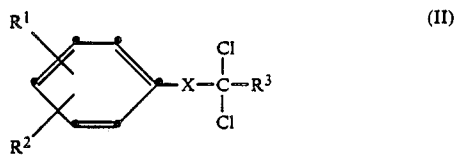

(II)

wherein $R^1$, $R^2$, $R^3$ and X are as defined for formula III, with hydrogen fluoride, in the presence of a catalytic amount of an antimony(V) compound.

22. The process of claim 6 wherein said antimony (V) halide is used in an amount of 5 to 10 mole %.

23. The process of claim 10 wherein said reaction is carried out at normal pressure.

* * * * *